(12) United States Patent
Wilkie

(10) Patent No.: US 6,811,701 B2
(45) Date of Patent: Nov. 2, 2004

(54) FIXED-FILM ANAEROBIC DIGESTION OF FLUSHED MANURE

(75) Inventor: Ann C. Wilkie, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 36 days.

(21) Appl. No.: 10/277,486

(22) Filed: Oct. 22, 2002

(65) Prior Publication Data

US 2003/0075501 A1 Apr. 24, 2003

Related U.S. Application Data

(60) Provisional application No. 60/335,065, filed on Oct. 24, 2001.

(51) Int. Cl.[7] .............................. C02F 3/28; C05F 3/00; C05F 5/00

(52) U.S. Cl. ....................... 210/603; 210/615; 210/196; 435/262.5; 71/10; 71/21

(58) Field of Search ................................ 210/603, 615, 210/194, 196; 71/10, 21; 435/262, 262.5

(56) References Cited

U.S. PATENT DOCUMENTS

| | | |
|---|---|---|
| 3,402,103 A | 9/1968 | Herman et al. |
| 3,846,289 A | 11/1974 | Jeris et al. |
| 3,956,129 A | 5/1976 | Jeris et al. |
| 4,009,099 A | 2/1977 | Jeris |
| 4,026,082 A | 5/1977 | Crofoot |
| 4,183,809 A | 1/1980 | Klapwijk et al. |
| 4,284,508 A | 8/1981 | Jewell |
| 4,366,059 A | 12/1982 | Witt et al. |
| 4,530,762 A | 7/1985 | Love |
| 4,561,974 A * | 12/1985 | Bernard et al. ............. 210/151 |
| 4,599,168 A | 7/1986 | Benjes et al. |
| 4,604,361 A * | 8/1986 | Peters ..................... 435/299.1 |
| 4,627,917 A * | 12/1986 | Morper ....................... 210/617 |
| 4,632,758 A | 12/1986 | Whittle |
| 4,780,198 A | 10/1988 | Crawford et al. |

(List continued on next page.)

FOREIGN PATENT DOCUMENTS

FR 2552298 * 3/1985

OTHER PUBLICATIONS

Mills, B., "Digester gobbles up odors" *Dairy Today*, Jan. 2000, pp. 17–18.
Wilkie, A. et al., "Start–up of anaerobic filters containing different support materials using pig slurry supernatant" *Biotechnology Letters*, 1984, vol. 6, No. 11, pp. 735–740.

(List continued on next page.)

*Primary Examiner*—Fred G. Prince
(74) *Attorney, Agent, or Firm*—Saliwanchik, Lloyd & Saliwanchik

(57) ABSTRACT

An apparatus for the fixed-film anaerobic digestion of flushed livestock manure includes an enclosed digester tank (fixed or flexible roof), internal media for biofilm development, a biogas collection and flare system, various pumps, and hydraulic control systems. The preferred media has substantially vertically-oriented, uninterrupted channels to promote enhanced bacterial attachment and biofilm development. The immobilization of microbial biomass within the reactor as a biofilm allows effective treatment of the wastewater at ambient and higher temperatures, as well as reasonable hydraulic retention times. The composition and concentration of bacterial groups in the biofilm developed on the media in the fixed-film digester result in a significantly enhanced anaerobic degradation process. This novel fixed-film digester design expands the potential application of anaerobic digestion to dilute livestock waste with significant levels of suspended solids. This holistic manure treatment system not only stabilizes the wastewater but also produces energy (biogas), controls odors, reduces pathogens, minimizes environmental impact from waste emissions, and maximizes fertilizer and water recovery for reuse.

56 Claims, 1 Drawing Sheet-

U.S. PATENT DOCUMENTS

| | | | |
|---|---|---|---|
| 5,096,579 A | | 3/1992 | Jordan et al. |
| 5,205,935 A | | 4/1993 | Ruocco |
| 5,228,995 A | * | 7/1993 | Stover .................. 210/603 |
| 5,232,585 A | | 8/1993 | Kanow |
| 5,389,248 A | | 2/1995 | Pare et al. |
| 5,419,833 A | | 5/1995 | Ely et al. |
| 5,500,112 A | | 3/1996 | McDonald |
| 5,518,620 A | | 5/1996 | Eguchi et al. |
| 5,560,819 A | | 10/1996 | Taguchi |
| 5,630,942 A | * | 5/1997 | Steiner .................. 210/603 |
| 6,126,816 A | | 10/2000 | Ruiz, Jr. |
| 6,183,643 B1 | * | 2/2001 | Goodley ................. 210/605 |
| 6,217,759 B1 | * | 4/2001 | Kolesnikov et al. ........ 210/194 |
| 6,254,775 B1 | | 7/2001 | McElvaney |
| 6,291,232 B1 | | 9/2001 | Miller, III |
| 6,299,774 B1 | | 10/2001 | Ainsworth et al. |

OTHER PUBLICATIONS

Wilkie, A. et al., "Pilot–scale digestion of pig slurry supernatat using an upflow anaerobic filter" *Environmental Technology Letters*, vol. 7, pp. 65–76, 1986.

Wilkie, A. et al., "The Development of the Anaeorbic Fixed–Bed Reactor and Its Application to the Treatment of Agricultural and Industrial Wastes" *International Biosystems*, 1989, pp. 183–226.

Wilkie et al., "Anaerobic digestion for odor control" *Nuisance Concerns in Animal Manure Management: Odors and Flies*, 1995, pp. 56–62.

"Show Me Results[2] Success Stories from the Florida Energy Office" *Florida Department of Community Affairs*, 1998–99.

Wilkie, A. et al., "Anaerobic digestion: holistic bioprocessing of animal manures" *Proceedings of the Animal Residuals Management Conference, 2000*, pp. 1–12.

Wilkie, A. et al., "Reducing dairy manure odor and producing energy" *Biocycle Journal of Composting & Organics Recycling*, 2000, pp. 48–50.

Hunter, Ed. "Sweet smell of success: New UF system helps dairy farms reduce odors," *UF News* http://www.napa.ufl.edu/2000news/sweetsme.htm.

* cited by examiner

FIXED-FILM ANAEROBIC DIGESTION OF FLUSHED MANURE

CROSS-REFERENCE TO RELATED APPLICATIONS

This application claims the benefit of provisional patent application Ser. No. 60/335,065, filed Oct. 24, 2001, which is hereby incorporated by reference in its entirety.

BACKGROUND OF THE INVENTION

The invention relates to an apparatus for lowering odors and recovering biogas from flushed livestock manure and, more specifically, to a closed system apparatus that provides for the fixed-film anaerobic digestion of flushed manure.

Anaerobic digestion of livestock manure has been implemented for many years. In anaerobic digestion, a mixed culture of bacteria mediates the degradation of the putrescible fraction of organic matter ultimately to methane, carbon dioxide and mineralized nutrients. Upon storage, livestock manure begins this process of degradation resulting in the production of intermediate compounds, which are volatile and often a source of odors. Since methanogenic microorganisms grow slowly and are present in limited numbers in fresh manure, these volatile intermediates accumulate in stored manure. In an effective anaerobic digester, the growth of methanogens is promoted such that the intermediate compounds are converted to biogas and nutrients, and the odor potential of the manure is greatly reduced.

The principal means for promoting methanogenic growth in anaerobic digestion of manure are controlling the operating temperature and/or controlling the residence time of the bacteria within the process. The types of anaerobic digester that have been implemented in the digestion of manure are rather limited due to the nature of manure as a substrate. The digester types have included variations of batch and semi-continuous processes, which include plug-flow digesters, complete-mix digesters, covered lagoons and a few demonstrations of mixed reactors with flexible-film support media (U.S. Pat. Nos. 5,096,579; 6,254,775). Except for covered lagoons, these manure digesters are usually operated at mesophilic temperatures (usually 35° C.), which requires energy input. Often a portion of the biogas is used to heat the manure slurry to the operating temperature. The requirement for heating dictates that the manure slurry fed to these reactors should have as high a total solids (TS) content as possible to minimize the water content which must be heated. In practice, the manure slurry added to these heated digesters should have a TS content of 4–12%. In temperate climates, often manure slurry with 1% TS or less will fail to provide enough biogas to heat the slurry to 35° C.

Without any support media for bacterial residence/attachment, plug-flow and complete-mix manure digesters rely on the hydraulic retention time (HRT) to control the solids residence time sufficiently to promote methanogenic growth. At mesophilic temperatures, effective treatment dictates that the HRT be maintained at greater than 10 days and, in practice, a 20–40 day HRT is common. The volume of the digester is directly proportional to the chosen HRT and the volumetric rate of manure production. Again, like temperature, the long HRT requirements of these manure digesters dictate that feed manure slurries must have as high a TS content as possible to minimize excess water, which takes up digester volume and results in a higher digester volume requirement to achieve the design HRT.

Currently, many livestock facilities use large volumes of water for barn flushing, resulting in excessive amounts of dilute wastewater (<1% TS). This effectively precludes these operations from using conventional plug-flow and complete-mix manure digesters due to both the uneconomical digester volume requirements and the excessive energy required to heat the dilute manure to mesophilic temperatures for effective digestion. Ideally, an anaerobic digestion apparatus for effective treatment of flushed manure should be able to operate at ambient temperatures, tolerate much shorter HRTs, and handle small amounts of fibrous solids.

Fixed-film anaerobic digesters use an internal support media to provide large surface areas for bacterial attachment. Thus, a greater concentration of bacteria is available to mediate the degradation of organic matter. This allows bacterial residence time to be maintained independently of the HRT of the liquid phase. Using much higher concentrations of attached bacteria allows fixed-film digesters to operate at much shorter HRTs and at much lower temperatures while achieving similar treatment efficiencies as conventional plug-flow and complete-mix systems. Currently, designs for high-rate anaerobic processing systems that use fixed-film digesters are available. However, none of the existing fixed-film designs are suitable for wastewaters with significant levels of suspended solids, such as those found in flushed manure. Suspended solids loading for existing fixed-film reactors are limited to less that 10% of the influent chemical oxygen demand (COD).

Livestock manure often includes materials used for bedding, such as hay, sawdust or sand. Often, such materials are poorly degraded or non-biodegradable. Where manure is in liquid form, the liquid is often conveyed into a "lagoon" after separation using solid-liquid separation equipment, with the resultant solids spread on land. Manure presents a complex substrate for anaerobic digestion because the volatile solids content is comprised of readily digestible soluble materials; fine particles that have a high surface-to-volume ratio and are readily accessible to bacterial enzymes; and larger fibrous particles that are relatively inaccessible to microbial attack. These larger fibrous particulates can contribute to clogging of packing material or media. The larger fibrous particulates can also hinder the attachment of bacteria to the media. Ultimately, these situations can lead to short-circuiting of the anaerobic system, which reduces the effectiveness of the biological treatment system. In addition, scum formation is a problem as well as blockage of pipes and other ancillary equipment caused by floating and suspended solids.

For example, certain anaerobic processing systems, such as those disclosed in U.S. Pat. No. 4,183,809, provide for anaerobic microorganisms suspended in a liquid medium to which wastewater is fed. Such processing systems, also known as upflow anaerobic sludge blanket (UASB) reactors, rely on the tendency of anaerobic microorganisms to form flocs or granules (sludge) which are retained within the system by an efficient gas/solids/liquid separation device. Unfortunately, with this system, the microorganisms may be washed out along with the effluent when high levels of particulates are contained in the wastewater. Because of this and the fact that it is difficult to obtain granular sludge with flushed manure, these systems have not been implemented for managing livestock manure.

In other anaerobic processing systems known as fluidized or expanded-bed reactors, the microorganisms are retained within the processing system by attachment to small inert particles (or "packing material"). Suitable particles include sand, anthracite, granular activated carbon, PVC particles, or diatomaceous earth. For example, U.S. Pat. Nos. 3,846,289, 3,956,129, 4,009,099, 4,284,508, and 5,232,585 disclose methods and apparatuses for denitrifying wastewater using solid particulate carriers where particle size generally ranges from about 0.2 to 3 millimeters. Such systems, however, suffer from washout of media and/or reduced media separation efficiency when wastes with suspended solids are treated.

Additional known anaerobic processing systems immobilize the microorganisms on a matrix within the reactor, called fixed-bed reactors. As disclosed in U.S. Pat. Nos. 4,366,059, 4,530,762, 4,561,168, and 4,599,168, the matrix is composed of an inert packing material, or "media," to provide a surface for microorganism attachment and biofilm development. Unlike the fluidized system and the expanded-bed systems described above, the media includes sheet, ring, or spherical material configured in either a random-pack or an oriented arrangement.

Random-pack (or "loose-fill") media include such materials as gravel, wood chips, or special plastic pieces designed with a high "surface to volume" ratio and are packed in loose-fill configuration in fixed-bed reactors. For example, U.S. Pat. Nos. 4,366,059, 4,780,198, and 5,419,833 disclose random-pack media of plastic rings or cylinders. As with the expanded-bed reactors, the random-pack media have poor hydraulic properties when applied to flushed manure. In particular, random-pack materials tend to clog quickly due to the recalcitrant suspended solids often found in flushed manure (e.g., animal hairs, grain husks, fibrous particles and inorganic precipitates) which causes the wastewater to cease to flow evenly through the media, reducing the effective treatment capacity.

In contrast, oriented (or "ordered") media provide improved hydraulic properties with certain waste products. Known oriented media include materials such as those disclosed in U.S. Pat. Nos. 4,530,762, 4,599,168, 5,228,995, and 6,126,816 for perforated PVC sheets, which are configured in modular blocks with cross-flowing channels located within the blocks. Although current oriented media provide improved hydraulic properties compared to those systems described above, oriented media still tend to suffer from the problem of clogging with respect to aqueous wastes that have significant levels of suspended solids, such as flushed manure. These modular block media promote the settling of suspended particles by decreasing the vertical distance the particles must travel before striking a surface. This promotes accumulation of solids on the media, which impairs biofilm interaction with the wastewater.

Anaerobic digesters with flexible film media and mechanical agitation for flushing/mixing within the system to address the issue of clogging in media have been described (U.S. Pat. Nos. 5,096,579; 6,254,775). These systems are designed for manure with 8–10% TS and are not applicable to flushed livestock waste. Also, these systems operate at a HRT of 28–30 days. Thus, no anaerobic fixed-film bioreactor system currently exists that can effectively treat flushed livestock manure.

BRIEF SUMMARY OF THE INVENTION

The subject invention provides an apparatus and method for the efficient fixed-film anaerobic digestion of flushed or diluted livestock manure. It is a further object of the present invention to provide a closed system apparatus and method for dilute manure digestion to reduce odors associated with livestock production while enabling ease of maintenance.

It is a still further object of the present invention to provide a closed system apparatus and method for manure digestion that reduces and/or eliminates clogging of the fixed-film media as well as accumulation of solids within the apparatus. In a related object, the present invention can operate efficiently for long periods of time, without requiring cleaning or purging of solid waste from the closed system apparatus.

It is a still further object of the present invention to provide a closed system apparatus and method for managing livestock manure wherein the livestock manure is treated at ambient temperatures to generate a usable biogas.

It is a still further object of the present invention to provide a closed system apparatus and method for manure digestion that operates effectively at relatively short hydraulic retention times.

It is a still further object of the present invention to provide a closed system apparatus and method for manure digestion wherein the livestock manure can be fed into either the upper or the lower region of the apparatus.

It is a still further object of the present invention to provide a closed system apparatus and method for manure digestion that reduces the emission of methane, a greenhouse gas.

It is a still further object of the present invention to provide a closed system apparatus and method for managing livestock manure that provides ease of inspection and maintenance of media structure.

It is a still further object of the present invention to provide a closed system apparatus and method for manure digestion to reduce the levels of pathogens in livestock waste.

It is a still further object of the present invention to provide a closed system apparatus and method for manure digestion to generate solid and liquid fertilizer with increased nutrient availability (i.e. nitrogen and phosphorus).

It is a still further object of the present invention to provide a closed system apparatus and method for manure digestion to generate recycled water for flushing livestock waste or for crop production.

Further objects and advantages of the present invention will become apparent by reference to the following description of the preferred embodiment and appended drawings.

The present invention includes a closed digester tank that has an influent and effluent line, internal media to house the anaerobic microorganisms, and a means for collecting and distributing biogas.

In a specific embodiment, the digester includes an influent line that can deliver livestock waste to either a lower zone or an upper zone of the digester tank. Further, the digester tank employs a support media to immobilize bacteria that has continuous void spaces in the form of channels that are substantially uninterrupted and vertically oriented. Examples of such channels include straight corrugated or non-corrugated vertical tubes having a horizontal cross-sectional area that is substantially circular or rectangular in shape. The digester tank can also include a means for the treated livestock waste, that has been suitably cleansed and purified, to exit from either the lower or upper zone of the tank. A portion of the treated livestock waste can also be recycled back into the influent line to promote more uniform biofilm development and activity. A further embodiment provides a means for re-circulating settled solids back into the tank to provide an agitation means for preventing the "bridging" of accumulated solids within the lower region of the tank. "Bridging" refers to the solidified sludge formed as a result of settling and interweaving of large particulates.

The gases generated by the anaerobic digestion of the livestock waste are captured and removed at the upper portion of the tank. These gases can be flared to burn off the excess methane or used to produce energy, such as heat or electricity.

As a completely closed system, the fixed-film anaerobic digester tank allows for the thorough anaerobic digestion and conversion of odorous organic intermediates found in stored manure into less offensive compounds. The composition and concentration of bacterial groups in the biofilm developed on the media in the subject invention result in a significantly enhanced anaerobic degradation process. Further, the subject invention provides a fixed-film anaerobic digester that functions effectively at ambient temperatures and short HRTs. Typically, fixed-film anaerobic digestion of livestock manure commences after pretreatment of flushed manure. Pretreatment can include mechanical screening and/or gravity settling. The pretreated flushed livestock waste is then directed into the subject digester tank.

DETAILED DISCLOSURE OF THE INVENTION

Figure 1:
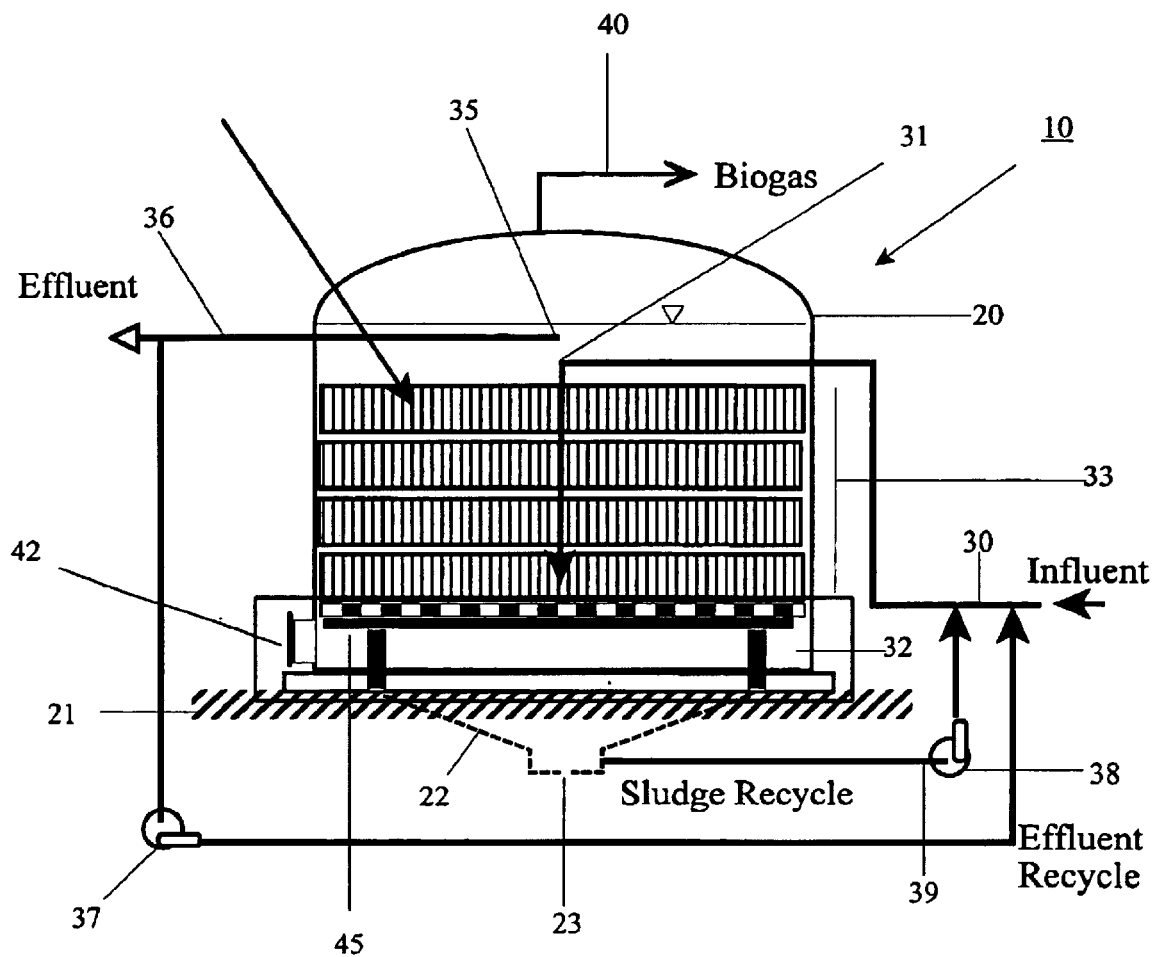
FIG. 1 is a perspective view of an apparatus according to the present invention illustrating the cycle of the system.

The fixed-film anaerobic digestion system according to the present invention includes a closed digester tank, a biogas collection system, an influent and effluent line and feed pump, and media inside the tank providing substantially vertically-oriented, uninterrupted channels of roughly 2–6 inches in diameter. The subject digestion system can advantageously treat flushed livestock manure at ambient temperatures while producing a source of energy. Further, the digestion system provides effective treatment of livestock waste at reasonable hydraulic retention times while effectively reducing pathogen levels as well as odors in the treated waste.

As used herein, the terms "anaerobic microorganism" and "bacteria" can be used interchangeably and refer to those organisms that anaerobically degrade organic matter.

As used herein, the term "biogas" refers to the gases produced as a result of the anaerobic degradation of flushed livestock waste according to the subject invention. Examples of biogas components include methane ($CH_4$), carbon dioxide ($CO_2$), and hydrogen sulfide ($H_2S$).

As used herein, the term "flushed livestock waste" refers to livestock manure that has been subjected to dilution with water. Often, flushing of livestock waste assists in the transportation and application of the waste. It is also possible to create "flushed livestock manure" from sand separation and washing systems. In an embodiment, flushed livestock waste contains 0–5% suspended solids.

As used herein, the term "livestock" refers to all domesticated animals, including horses, swine, all varieties of cattle such as dairy cows, steer, yak, goats, or any animals whose waste is subject to dilution with water for conveyance or processing.

As used herein, the term "media" refers to an inert packing material placed inside the digester tank that provides a surface area to support bacterial attachment and biofilm development.

As used herein, the term "pretreatment" refers to the substantial removal of materials including, for example, inorganic material such as sand, and fibrous materials that are relatively indigestible anaerobically. Removal of such materials from flushed livestock waste can be performed using common methods such as gravity settlement and/or mechanical screening. According to the present invention, the pretreated flushed livestock waste provides a suitable substrate for efficient and productive anaerobic digestion. In a preferred embodiment, the pretreated flushed livestock waste is dairy manure containing less than 1% suspended solids or biologically inert materials. The subject invention can also be used to treat the filtrate/product of any process or combination of processes that render livestock manure to contain 0–5% suspended solids.

As used herein, the term "sludge" refers to those solids, including biologically inert materials, that remain in the digester after flushed livestock waste has been subjected to anaerobic digestion, in accordance with the present invention. Sludge can also include readily digestible materials and/or fine particles readily accessible to bacterial enzymes that were not fully degraded according to the present invention.

As used herein, the term "treated waste" refers to flushed livestock waste that has been subjected to anaerobic digestion according to the present invention.

In the digester tank, immobilization of bacteria as a biofilm on a media serves to prevent washout of slower growing cells and provide biomass retention independent of hydraulic retention time. Because more bacteria are available for a given reactor volume as compared to conventional suspended-growth designs and covered anaerobic lagoons used to treat livestock waste, less time is needed to degrade the flushed livestock waste, allowing operation at short hydraulic retention times typically in the range of 2–6 days.

Further, the subject media immobilizes the microbial biomass within the digester tank to allow effective treatment of the flushed livestock waste at ambient temperatures. The temperature of the flushed manure influences the organic loading rate applied to the digester. Table I gives a range of recommended organic loading rates over a range of temperatures. As understood by the skilled artisan, the temperature of the flushed manure can be higher than 35° C. The high loading rates serve to maximize biogas production while the lower loading rates maximize treatment efficiency.

TABLE I

Recommended organic loading rates based on manure wastewater temperatures.

| Wastewater temperature ° C. | Recommended organic loading rates | |
|---|---|---|
| | Low g COD/L/d | High g COD/L/d |
| 15 | 0.2 | 1 |
| 20 | 0.5 | 3 |
| 25 | 1 | 4 |
| 30 | 1.5 | 6 |
| 35 | 2 | 8 |

The media, according to the present invention, are oriented media. The media includes substantially vertically-oriented, uninterrupted channels of roughly 2–6 inches in diameter. The subject media uniquely reduces the likelihood of clogging associated with dilute wastewaters containing significant levels of suspended solids by allowing fine suspended solids to pass freely through the media. In an embodiment, the media includes straight corrugated or non-corrugated vertical tubes having a horizontal cross-sectional area that is substantially circular or rectangular in shape. In a preferred embodiment, the media includes straight corrugated vertical tubes having a horizontal cross-sectional area that is substantially circular. For example, thermal plastic pipe (PE, PVC, PP, ABS, etc.) can be employed as the oriented media in the fixed-film digester.

The influent line directs either flushed livestock waste or pretreated flushed livestock waste to the digester tank. The influent line can provide flushed livestock waste to the digester tank at either an upper or a lower region in the tank. In a preferred embodiment, the influent line provides flushed livestock waste to the lower region of the tank to supply an upflow system. In another embodiment, the influent line provides flushed livestock waste to the upper region of the digester tank to present a downflow system.

The effluent line removes the treated waste from the digester tank. In an embodiment, the effluent line removes the treated waste and recycles a portion of the treated waste back into the influent line through a recycle pump. The excess treated waste is conveyed to a storage pond.

By recycling the treated waste, the frequency of contact between the bacterial cells and the media in the fixed-film digester is increased, thereby creating an environment conducive to more uniform biofilm development and activity. This is significant when diffusion of substrates and nutrients into a biofilm is considered. Faster biofilm development allows for quicker commissioning of the reactor by reducing the time taken for the start-up phase. Also, treatment of the wastewater is more rapid due to faster uptake of substrates through a more evenly distributed biofilm.

An embodiment of the subject invention includes a digester tank with a conical-shaped bottom. The conical bottom serves to accumulate suspended solids and provides access space for inspection and maintenance below the media. The conical-shaped bottom collects any sludge at the apex of the bottom. The collected sludge can be recycled using a recycle pump and line into the influent line. Alternatively, the collected sludge can be removed and applied to land as fertilizer.

The digester system according to the present invention includes an access hatch that (see FIGS. 1, 42) that provides ease of inspection and maintenance below the media.

The system typically produces biogas at 80–90% methane ($CH_4$) and 10–20% carbon dioxide ($CO_2$), depending on organic loading rate, temperature and HRT. For every kilogram of chemical oxygen demand (COD) of waste converted by the process, 0.35 $m^3$ of $CH_4$(dry gas at 0° C. and 1 atm) is produced. The biogas produced from the digester can be flared to further reduce odors and emissions of methane, a potent greenhouse gas. Potential options for biogas utilization include use as a fuel to produce heat, electricity, or motive force (for example: production of hot water; generation of electricity for on-farm use; absorption refrigeration; and vehicular fuel).

Capital costs are one impediment to the implementation of current anaerobic digestion technologies to treat flushed manure. In particular, media used in fixed-film anaerobic digesters can be a significant portion of the cost in constructing these systems. Thus, the selection of an oriented media, which is widely available and relatively low in cost, is preferred for reducing economic barriers to the implementation of this technology.

The media in the fixed-film digester is raised on a support structure (see FIGS. 1, 45). This provides space below the media for accumulation and removal of recalcitrant suspended solids. This eliminates the potential for clogging and short-circuiting and at the same time allows for inspection and maintenance below the media via the access hatch. The media, which can be buoyant, can also be secured by a media support structure positioned above the media.

Fixed-film digesters are ideally suited for treating large volumes of dilute wastewaters, such as those generated by dairy and swine operations, because large numbers of bacteria can be concentrated inside smaller digesters operating at shorter hydraulic retention times than would be needed to achieve the same degree of treatment with conventional suspended-growth anaerobic reactors and covered anaerobic lagoons. Further, fixed-film digesters have a smaller footprint—an important factor where land availability is limited. Also, from an aesthetic perspective, a compact digester design is preferable to large lagoons.

In addition to minimizing offensive odors and producing usable energy, anaerobic digestion has several other important benefits. One advantage is nearly complete retention in the digester effluent of the fertilizer nutrients (nitrogen, phosphorous, and potassium) that are in the raw manure entering the digester. Organically bound nutrients are mineralized to soluble forms during the anaerobic digestion process—transforming valuable plant nutrients into a more predictable fertilizer product. Also, a broad spectrum of microbial pathogens is destroyed by anaerobic digestion. This may have particular significance for animal health by providing cleaner water for use in recycled flush systems. The potential of the subject fixed-film digester to provide treated wastewater for recycle flushing is especially valuable as water becomes an increasingly precious limited resource.

As will be apparent to the ordinary skilled artisan in view of this disclosure, the fixed-film anaerobic digester can also be applied for treatment of other agricultural and industrial wastewaters. Examples of other wastewaters include: food processing, brewery, distillery, winery, pharmaceutical, cannery, cheese processing, potato processing, pulp and paper, and yeast production. The subject digester system can also be applied to municipal wastewater.

Following are examples which illustrate procedures for practicing the invention. These examples should not be construed as limiting. All percentages are by weight and all solvent mixture proportions are by volume unless otherwise noted.

EXAMPLE 1

Referring now to FIG. 1, a preferred embodiment of a fixed-film anaerobic digester for treatment of flushed livestock manure is illustrated and generally designated by the reference numeral 10. The basic fixed-film digester design 10 consists of a tank 20 filled with plastic media 34 on which a consortium of bacteria (not shown) attach and grow as a slime layer or biofilm (not shown). The closed digester tank 20 consists of a cylindrical (approximately 1:1 height to diameter), glass-lined bolted-steel tank, but can be constructed of other suitable materials and in other shapes, as commonly understood by those skilled in the art.

The media 34 in the fixed-film digester is preferably constructed of vertically arranged, 3 in. diameter, corrugated polyethylene drainage pipe, similar to that commonly used in septic tank drain fields. The media is preferably installed in four layers of 4 ft. pipe 33 and occupies approximately ⅔ of the tank height. In practice, the media can be configured in single or multiple layers, and pipe sizes and composition can be modified as desired for the particular project. Polyethylene pipe is a widely available, light-weight material which offers a low-cost solution to providing sufficient surface area in the digester for microbial attachment and biofilm development, and is not prone to clogging. With modular and random-pack media, there are multiple points throughout the media-bed where fibrous manure solids can accumulate, whereas only the bottom and top edges of the subject pipe media can accumulate fibers.

Table II lists some preferred properties of the media and the tank. Alternatively, the digester tank can be any size and shape appropriate for the efficient treatment of flushed livestock waste, as commonly understood by those skilled in the art. Also, the closed gas-tight tank can have either a fixed or a flexible roof.

TABLE II

Example Tank and Media Properties

| Tank type | bolted glass fused to steel | cylindrical |
|---|---|---|
| Tank height | ft | 25.7 |
| Tank diameter | ft | 25 |
| Total volume | $m^3$ | 408 |
| Active liquid volume | $m^3$ | 369 |
| Media volume | $m^3$ | 225 |
| Tank aspect ratio | height/width | 1.03 |
| Media height to tank height | height/height | 0.62 |
| Media polymer | 3" corrugated plastic pipe | polyethylene |
| Media density | $kg/m^3$ | 954 |
| Media porosity | $L/L_m$ | 0.978 |
| Active specific surface area | $m^2/m^3$ media volume | 74 |
| Influent areal dispersion | $m^2$/inlet | 46 |

The digester tank 20 is set on a custom-designed slab 21 that preferably has a conical bottom 22 for easy removal or recycling of sludge.

Following pretreatment by mechanical screening and/or gravity settling, the influent wastewater is pumped through the influent line 30 from a sump (not shown). The influent line 30 runs through the wall of the tank 20. The wastewater flows down through the influent line 31 into the holding area 32 below the media zones 33. The wastewater then travels up through the media zones 33.

The treated wastewater flows out of the effluent line 35–36. A portion of the effluent is recycled through a pump 37 back to the influent line 30. Normally, a 3:1 recycling ratio assures even concentrations across the media and even growth of the biofilm. The digested effluent flows to a storage pond (not shown) to be land applied in accordance with a nutrient management plan. A desludging pump 38 removes sludge via the sludge recycle line 39 leading from the apex of the conical bottom 23 and recycles it back into the influent line 30. In an alternate embodiment, some of the sludge can be recycled directly back into the conical bottom to provide an additional means for preventing the "bridging" of accumulated solids within the lower region of the tank.

Biogas leaves the upper region of the digester tank 40 and passes through a sediment trap (not shown) to a mass flow meter (not shown), prior to flowing through a pressure regulator (not shown) and on to the flare (not shown). Both pressure and vacuum emergency relief valves (not shown) are located on the upper region of the tank 20. The biogas produced can be collected and used, for example, either directly (e.g., for heating water) or in an engine generator to provide electricity. The tank also has several sampling ports (not shown) for obtaining mixed liquor samples at various radii from above, below, and within each media zone 33.

Table III gives some sample characteristics of flushed dairy manure before and after pretreatment as found during demonstration of the apparatus.

TABLE III

Example flushed dairy manure characteristics

| Parameter | Units | Concentration |
|---|---|---|
| Before separation | | |
| TS | mg/L | 9837 |
| VS | mg/L | 9722 |
| CODt | mg/L | 9745 |
| After mechanical separation and sedimentation | | |
| TS | mg/L | 5243 |
| VS | mg/L | 3850 |
| TSS | mg/L | 2806 |
| CODt | mg/L | 5613 |
| CODs | mg/L | 1900 |
| pH | pH units | 7.45 |

Table IV illustrates sample operating conditions of an apparatus in accordance with the subject invention for three different conditions.

TABLE IV

Example of three operating conditions for flushed dairy manure digestion

| Parameter | I | II | III |
|---|---|---|---|
| Temperature (° C.) | 29 | 29 | 18 |
| HRT (d) | 3 | 2 | 3 |
| Influent COD (mg/L) | 4609 | 4819 | 5613 |
| Influent soluble COD (mg/L) | 1924 | 2310 | 1900 |
| Organic loading rate (g COD/L/d) | 1.54 | 2.41 | 1.87 |
| COD reduction (%) | 48 | 44 | 40 |
| Soluble COD reduction (%) | 69 | 62 | 49 |
| $CH_4$ Production Rate ($L/L_r$/d @ STP) | 0.26 | 0.37 | 0.26 |

Inasmuch as the preceding disclosure presents the preferred embodiment devised by the inventor for practicing the invention and is intended to enable one skilled in the pertinent art to carry it out, it is apparent that methods incorporating modifications and variations will be obvious to those skilled in the art. As such, it should not be construed to be limited thereby but should include such aforementioned obvious variations and be limited only by the spirit and scope of the following claims.

I claim:

1. A fixed-film anaerobic system for treating flushed livestock waste comprising:
   a. a closed digester tank having a floor and a roof, and having an upper and a lower region;
   b. a media supported within the digester tank comprising substantially vertically-oriented, uninterrupted channels to immobilize anaerobic microorganisms;
   c. an influent line to direct the flushed livestock waste into the digester tank;
   d. an effluent line to remove treated flushed livestock waste from the digester tank;
   e. an access hatch to facilitate inspection and maintenance below the media; and
   f. a means for collecting biogas produced as a by-product of anaerobic digestion of the flushed livestock waste.

2. The system according to claim 1, wherein the media are 2–6 inch diameter thermal plastic pipes with circular cross-sections.

3. The system according to claim 1, wherein the effluent line recycles a selected amount of the treated flushed livestock waste back into the influent line.

4. The system according to claim 1, wherein the flushed livestock waste is pretreated flushed livestock waste.

5. The system according to claim 1, wherein the media is raised from the lower region of the digester tank on a support structure that allows for inspection and maintenance below the media.

6. The system according to claim 1, wherein the digester tank has a conical-shaped bottom.

7. The system according to claim 1, wherein the influent line directs the flushed livestock waste into the lower region of the digester tank to operate an upflow system.

8. The system according to claim 1, wherein the influent line directs the flushed livestock waste into the upper region of the digester tank to operate a downflow system.

9. The system according to claim 1, further comprising a means for removing sludge from the lower region of the digester tank.

10. The system according to claim 9, wherein the means for removing the sludge recycles the sludge back into the influent line.

11. The system according to claim 9, wherein the means for removing the sludge recycles the sludge back into the lower region of the digester tank.

12. The system according to claim 1, wherein the biogas is flared.

13. The system according to claim 1, wherein the biogas is used for energy.

14. The system according to claim 1, wherein the digester tank is operated at ambient temperatures.

15. The system according to claim 1, wherein the digester tank is heated above ambient temperature.

16. The system according to claim 1, wherein the flushed livestock waste is combined with other agricultural and/or industrial wastewaters.

17. The system according to claim 1, wherein the flushed livestock waste is at a temperature of 25° C. and the flushed livestock waste has an organic loading rate of 1 g COD/L/d.

18. The system according to claim 1, wherein the flushed livestock waste is at a temperature of 30° C. and the flushed livestock waste has an organic loading rate 1.5 g COD/L/d.

19. The system according to claim 1, wherein the flushed livestock waste is at a temperature of 25° C. and the flushed livestock waste has an organic loading rate 4 g COD/L/d.

20. The system according to claim 1, wherein the flushed livestock waste is at a temperature of 30° C. and the flushed livestock waste has an organic loading rate 6 g COD/L/d.

21. A fixed-film anaerobic system for treating wastewaters comprising:
   a. a closed digester tank having a floor and a roof, and having an upper and a lower region;
   b. a media supported within the digester tank comprising substantially vertically-oriented, uninterrupted channels to immobilize anaerobic microorganisms;
   c. an influent line to direct the wastewater into the digester tank;
   d. an effluent line to remove treated wastewater from the digester tank;
   e. an access hatch to facilitate inspection and maintenance below the media; and
a means for collecting biogas produced as a by-product of anaerobic digestion of the wastewater.

22. The system according to claim 21, wherein the wastewater is agricultural wastewater.

23. The system according to claim 21, wherein the wastewater is industrial wastewater.

24. The system according to claim 21, wherein the wastewater is municipal wastewater.

25. The system according to claim 21, wherein the wastewater is selected from the group consisting of food processing wastewater, brewery wastewater, distillery wastewater, winery wastewater, pharmaceutical wastewater, cannery wastewater, cheese processing wastewater, potato processing wastewater, pulp and paper wastewater, and yeast production wastewater.

26. A process for treating flushed livestock waste comprising:
   a. providing a closed digester tank having a floor and a roof, and having an upper and lower region; a media supported within the digester tank comprising substantially vertically-oriented, uninterrupted channels having a population of anaerobic microorganisms retained therein; an influent line; an effluent line; an access hatch to facilitate inspection and maintenance below the media; and a means for collecting biogas produced as a by-product of anaerobic digestion of the flushed livestock waste;
   b. directing the flushed livestock waste into the digester tank via the influent line;
   c. passing the flushed livestock waste through the media channels in the absence of oxygen for a sufficient time to allow the anaerobic microorganisms to digest the organic matter and produce biogas;
   d. collecting and discharging the biogas; and
   e. discharging the treated flushed livestock waste from the digester via the effluent line.

27. The process according to claim 26, further comprising the step of pre-treating the flushed livestock waste to remove a portion of the suspended solids.

28. The process according to claim 26, wherein the media are 2–6 inch diameter thermal plastic pipes with circular cross-sections.

29. The process according to claim 26, wherein the effluent line recycles a selected amount of the treated flushed livestock waste back into the influent line.

30. The process according to claim 26, wherein the media is raised from the lower region of the digester tank on a support structure that allows for inspection and maintenance below the media.

31. The process according to claim 26, wherein the digester tank has a conical-shaped bottom.

32. The process according to claim 26, wherein the influent line directs the flushed livestock waste into the lower region of the digester tank to operate an upflow system.

33. The process according to claim 26, wherein the influent line directs the flushed livestock waste into the upper region of the digester tank to operate a downflow system.

34. The process according to claim 26, further comprising a means for removing sludge from the lower region of the digester tank.

35. The process according to claim 34, wherein the means for removing the sludge recycles the sludge back into the influent line.

36. The process according to claim 34, wherein the means for removing the sludge recycles the sludge back into the lower region of the digester tank.

37. The process according to claim 26, wherein the biogas is flared.

38. The process according to claim 26, wherein the biogas is used for energy.

39. The process according to claim 26, wherein the digester tank is operated at ambient temperatures.

40. The process according to claim 26, wherein the digester tank is heated above ambient temperature.

41. The process according to claim 26, wherein the flushed livestock waste is at a temperature of 25° C. and the flushed livestock waste has an organic loading rate 1 g COD/L/d.

42. The process according to claim 26, wherein the flushed livestock waste is at a temperature of 30° C. and the flushed livestock waste has an organic loading rate of 1.5 g COD/L/d.

43. The process according to claim 26, wherein the flushed livestock waste is at a temperature of 25° C. and the flushed livestock waste has an organic loading rate of 4 g COD/L/d.

44. The process according to claim 26, wherein the flushed livestock waste is at a temperature of 30° C. and the flushed livestock waste has an organic loading rate of 6 g COD/L/d.

45. The process according to claim 26, wherein the flushed livestock waste is combined with other agricultural and/or industrial wastewaters.

46. A support media for anaerobic microorganism attachment in a fixed-film anaerobic digester for treating flushed livestock waste consisting of at least one layer of a plurality substantially vertically-oriented, uninterrupted channels about 2–6 inches in diameter.

47. The support media according to claim 46, wherein the uninterrupted channels are 3 inches in diameter.

48. The support media according to claim 46, wherein the uninterrupted channels are wholly non-corrugated vertical tubes.

49. The support media according to claim 46, wherein the uninterrupted channels are wholly corrugated vertical tubes.

50. The support media according to claim 46, wherein the uninterrupted channels have a horizontal cross-sectional area that is substantially circular.

51. The support media according to claim 46, wherein the uninterrupted channels are composed of thermal plastic pipes.

52. A process for treating wastewaters comprising:
   a. providing a closed digester tank having a floor and a roof, and having an upper and lower region; a media supported within the digester tank comprising substantially vertically-oriented, uninterrupted channels having a population of anaerobic microorganisms retained therein; an influent line; an effluent line; an access hatch to facilitate inspection and maintenance below the media; and a means for collecting biogas produced as a by-product of anaerobic digestion of the wastewater;
   b. directing the wastewater into the digester tank via the influent line;
   c. passing the wastewater through the media channels in the absence of oxygen for a sufficient time to allow the anaerobic microorganisms to digest the organic matter and produce biogas;
   d. collecting and discharging the biogas; and
   e. discharging the treated wastewater from the digester via the effluent line.

53. The process according to claim 52, wherein the wastewater is agricultural wastewater.

54. The process according to claim 52, wherein the wastewater is industrial wastewater.

55. The process according to claim 52, wherein the wastewater is municipal wastewater.

56. The process according to claim 52, wherein the wastewater is selected from the group consisting of food processing wastewater, brewery wastewater, distillery wastewater, winery wastewater, pharmaceutical wastewater, cannery wastewater, cheese processing wastewater, potato processing wastewater, pulp and paper wastewater, and yeast production wastewater.

* * * * *

UNITED STATES PATENT AND TRADEMARK OFFICE
CERTIFICATE OF CORRECTION

PATENT NO. : 6,811,701 B2
DATED : November 2, 2004
INVENTOR(S) : Ann C. Wilkie

It is certified that error appears in the above-identified patent and that said Letters Patent is hereby corrected as shown below:

Column 5,
Line 3, "flared to bum off" should read -- flared to burn off --

Column 13,
Lines 24 and 25, "plurality substantially" should read -- plurality of substantially --

Signed and Sealed this

Thirty-first Day of May, 2005

JON W. DUDAS
*Director of the United States Patent and Trademark Office*